United States Patent
Uchida et al.

(10) Patent No.: US 12,399,183 B2
(45) Date of Patent: Aug. 26, 2025

(54) BIOMARKERS FOR COGNITIVE DYSFUNCTION DISEASES AND METHOD FOR DETECTING COGNITIVE DYSFUNCTION DISEASE USING BIOMARKERS

(71) Applicants: MCBI INC., Tsukuba (JP); UNIVERSITY OF TSUKUBA, Tsukuba (JP)

(72) Inventors: Kazuhiko Uchida, Tsukuba (JP); Kohji Meno, Tsukuba (JP); Hideaki Suzuki, Tsukuba (JP); Yoshinori Nishimura, Tsukuba (JP)

(73) Assignees: MCBI INC., Tokyo (JP); UNIVERSITY OF TSUKUBA, Tsukuba (JP)

( * ) Notice: Subject to any disclaimer, the term of this patent is extended or adjusted under 35 U.S.C. 154(b) by 0 days.

(21) Appl. No.: 18/221,053

(22) Filed: Jul. 12, 2023

(65) Prior Publication Data
US 2024/0003913 A1   Jan. 4, 2024

Related U.S. Application Data

(62) Division of application No. 16/890,739, filed on Jun. 2, 2020, now abandoned, which is a division of application No. 14/901,275, filed as application No. PCT/JP2013/067785 on Jun. 28, 2013, now abandoned.

(51) Int. Cl.
G01N 33/68   (2006.01)
C07K 14/47   (2006.01)

(52) U.S. Cl.
CPC ......... *G01N 33/6893* (2013.01); *C07K 14/47* (2013.01); *G01N 2333/76* (2013.01); *G01N 2333/775* (2013.01); *G01N 2333/96433* (2013.01); *G01N 2800/2814* (2013.01)

(58) Field of Classification Search
CPC .......... G01N 33/6893; G01N 2333/76; G01N 2333/775; G01N 2333/96433; G01N 2800/2814; G01N 33/6896; G01N 2800/2821; C07K 14/47; C12N 15/115; C12N 2310/16; G06F 17/18
See application file for complete search history.

(56) References Cited

U.S. PATENT DOCUMENTS

| | | |
|---|---|---|
| 2008/0220013 A1 | 9/2008 | Hochstrasser et al. |
| 2015/0125876 A1 | 5/2015 | Uchida et al. |

FOREIGN PATENT DOCUMENTS

| | | |
|---|---|---|
| JP | 2004-333274 A | 11/2004 |
| JP | 2006-308533 A | 11/2006 |
| JP | 2009-501333 A | 1/2009 |
| JP | 2010-271078 A | 12/2010 |
| JP | 2012-37349 A | 2/2012 |
| JP | 2012-132808 A | 7/2012 |
| WO | WO2004/058052 A2 | 7/2004 |
| WO | WO 2007/007129 A2 | 1/2007 |
| WO | WO 2011/142778 A1 | 11/2011 |
| WO | WO 2012/086197 A1 | 6/2012 |
| WO | WO 2012/168561 A1 | 12/2012 |

OTHER PUBLICATIONS

Aisen et al., Cold Spring Harb Perspect Med; 2:a006395 (Year: 2012).*
Alyaz et al., "Complement Activation as a Biomarker for Alzheimer's Disease," Immunobiology, vol. 217, No. 2, 2012, pp. 204-215.
Alberio et al., "Parkinson's disease plasma biomarkers: An automated literature analysis followed by experimental validation," Journal of Proteomics (2013), vol. 90, pp. 107-114.
Alzheimer's Society, "How is mild cognitive impairment treated?", Retrieved from <https://www.alzheimers.org.uk/about-dementia/types-dementia/mild-cognitive-impairment-treatments#:~:text=There%20are%20currently%20no%20drugs,slow%20its%20progression%20to%20dementia>, retrieved on Apr. 13, 2022 (Year: 2022).
Andrade and Radhakrishnan, Indian J Psychiatry, Jan.-Mar. 2009; 51(1): 12-25 (Year: 2009).

(Continued)

*Primary Examiner* — Kimberly Ballard
*Assistant Examiner* — Stacey N MacFarlane
(74) *Attorney, Agent, or Firm* — Birch, Stewart, Kolasch & Birch, LLP (57) ABSTRACT

Biomarkers for detecting cognitive dysfunction diseases and methods for detecting cognitive dysfunction diseases using the biomarkers are provided. A method for detecting cognitive dysfunction diseases comprising measuring one or more biomarkers for detecting cognitive dysfunction diseases selected from the following (a), (b), and (c) in a biological sample simultaneously or separately: (a) a biomarker for detecting cognitive dysfunction diseases consisting of an intact protein of apolipoprotein A1 comprising the amino acid sequence represented by SEQ ID NO:1 or a partial peptide thereof; (b) a biomarker for detecting cognitive dysfunction diseases consisting of an intact protein of transthyretin comprising the amino acid sequence represented by SEQ ID NO:2 or a partial peptide thereof; and (c) a biomarker for detecting cognitive dysfunction diseases consisting of an intact protein of complement C3 comprising the amino acid sequence represented by SEQ ID NO:3 or a partial peptide thereof.

7 Claims, 3 Drawing Sheets
Specification includes a Sequence Listing.

(56) References Cited

OTHER PUBLICATIONS

Benkirane et al., "Antigenicity and Immunogenicity of Modified Synthetic Peptides Containing D-Amino Acid Residues; Antibodies to a D-Enantiomer Do Recognize the Parent L-Hexapeptide and Reciprocally," Journal of Biological Chemistry, vol. 268, No. 35, Dec. 15, 1993, pp. 26279-26285.
Bowling et al., "A logistic approximation to the cumulative normal distribution," Journal of Industrial Engineering and Management, vol. 2, No. 1, 2009, pp. 114-127.
Czepiel, "Maximum Likelihood Estimation of Logistic Regression Models: Theory and Implementation," http://czep.net/stat/mlelr.pdf, 2010, pp. 1-23.
Finehout et al., "Cerebrospinal fluid proteomic biomarkers for Alzheimer's disease," Ann Neurol, vol. 61, No. 2, Feb. 2007, 1 page, abstract provided only.
Finehout et al., "Cerebrospinal Fluid Proteomic Biomarkers for Alzheimer's Disease," Annals of Neurology, vol. 61, No. 2, Feb. 2007, pp. 120-129.
Harr et al., "Brain Expression of Apolipoproteins E, J, and A-I in Alzheimer's Disease," Journal of Neurochemistry, vol. 66, No. 6, 1996, pp. 2429-2435.
Ishii et al., "Alzheimer-byo to MCI ni Okeru Kessel Transthyretin Taryotai no Kaiseki," Dementia Japan, vol. 24, No. 3, Sep. 15, 2010, 4 pages.
Keeney et al., "Apolipoprotein A-I: Insights from redox proteomics for its role in neurodegeneration," Protomics Clin. Appl. (2013), vol. 7, pp. 109-122.
Korolainen et al., "An update on clinical proteomics in Alzheimer's research," Journal of Neurochemistry (2010), vol. 112, pp. 1386-1414.
Liu et al., "Proteomic Identification of Lower Apolipoprotein A-I in Alzheimer's Disease," Dement. Geriatr. Cogn. Disord. (2006), vol. 21, pp. 155-161.
Luminex® xMAP® technology brochure, published online 2015, retrieved from <chrome-extension://efaidnbmnnnibpcajpcglclefindmkaj/ https://www.sigmaaldrich.com/deepweb/assets/sigmaaldrich/product/c retrieved on Jan. 4, 2023 (Year: 2015).
Mayo Clinic, "Mild cognitive impairment (MCI)"; "Diagnosis and Treatment", retrieved from <https://www.mayoclinic.org/diseases-conditions/mild-cognitive-impairment/diagnosis-treatment/drc-20354583#:~:text=Mild%20cognitive%20impairment%20(MCI)>, retrieved on Apr. 13, 2022 (Year: 2022).
Nakano et al. (editors), "The better understanding of Alzheimer's disease (Yokuwakaru Alzheimer's Disease)," Nagai Shoten Co., Ltd., 2004, 27 pages.
Neuroscience ELISA Kits & MILLIPLEX MAP/MAG Assays, published by Millipore (Year: 2010).
Nyberg et al., "Proteomic Biomarkers for Acute Interstitial Lung Disease in Gefitinib-Treated Japanese Lung Cancer Patients," PLoS One, vol. 6, No. 7, e22062, 2011 (Published online Jul. 20, 2011), 16 pages.
Perrin et al., PLoS One, 6(1):e16032, 2011.
Saczynski et al., "The Relation Between Apolipoprotein A-I and Dimentia," Am. J. Epidemiol. (2007), vol. 165, No. 9, pp. 985-992.
Salloway S, Ferris S, Kluger A, Goldman R, Griesing T, Kumar D, Richardson S, for the Donepezil '401' Study Group, Efficacy of donepezil in mild cognitive impairment, Neurology 2004;63:651-657 (Year: 2004).
Song et al., "Plasma Apolipoprotiens as Biomarkers of Mild Cognitive Impairments in a Community-Based Sample," Alzheimer's & Dementia (Jul. 2011), vol. 7, No. 4, supplement, p. S146, P1-115.
Song et al., "Plasma biomarkers for mild cognitive impairment and Alzheimer's disease," Brain Research Reviews (2009), vol. 61, pp. 69-80.
Velayudhan et al., "Plasma Transthyretin as a Candidate Marker for Alzheimer's Disease," Journal of Alzheimer's Disease, vol. 28, 2012, pp. 369-375.
Wang et al., Am J Pathol, 178:1509-1516, 2011.
Williams et al., Evid Rep Technol Assess., Apr. 2010; (193): 1-727 (Year: 2010).
Zhang et al., Proteomics, 4:244-256, 2004.
U.S. Appl. No. 14/901,275, filed Dec. 28, 2015.
U.S. Appl. No. 16/890,739, filed Jun. 2, 2020.

* cited by examiner

SEQUENCE LISTING

```
Sequence total quantity: 3
SEQ ID NO: 1            moltype = AA   length = 267
FEATURE                 Location/Qualifiers
source                  1..267
                        mol_type = protein
                        organism = Homo sapiens
SEQUENCE: 1
MKAAVLTLAV LFLTGSQARH FWQQDEPPQS PWDRVKDLAT VYVDVLKDSG RDYVSQFEGS    60
ALGKQLNLKL LDNWDSVTST FSKLREQLGP VTQEFWDNLE KETEGLRQEM SKDLEEVKAK   120
VQPYLDDFQK KWQEEMELYR QKVEPLRAEL QEGARQKLHE LQEKLSPLGE EMRDRARAHV   180
DALRTHLAPY SDELRQRLAA RLEALKENGG ARLAEYHAKA TEHLSTLSEK AKPALEDLRQ   240
GLLPVLESFK VSFLSALEEY TKKLNTQ                                      267

SEQ ID NO: 2            moltype = AA   length = 147
FEATURE                 Location/Qualifiers
source                  1..147
                        mol_type = protein
                        organism = Homo sapiens
SEQUENCE: 2
MASHRLLLLC LAGLVFVSEA GPTGTGESKC PLMVKVLDAV RGSPAINVAV HVFRKAADDT    60
WEPFASGKTS ESGELHGLTT EEEFVEGIYK VEIDTKSYWK ALGISPFHEH AEVVFTANDS   120
GPRRYTIAAL LSPYSYSTTA VVTNPKE                                      147

SEQ ID NO: 3            moltype = AA   length = 1663
FEATURE                 Location/Qualifiers
source                  1..1663
                        mol_type = protein
                        organism = Homo sapiens
SEQUENCE: 3
MGPTSGPSLL LLLLTHLPLA LGSPMYSIIT PNILRLESEE TMVLEAHDAQ GDVPVTVTVH    60
DFPGKKLVLS SEKTVLTPAT NHMGNVTFTI PANREFKSEK GRNKFVTVQA TFGTQVVEKV   120
VLVSLQSGYL FIQTDKTIYT PGSTVLYRIF TVNHKLLPVG RTVMVNIENP EGIPVKQDSL   180
SSQNQLGVLP LSWDIPELVN MGQWKIRAYY ENSPQQVFST EFEVKEYVLP SFEVIVEPTE   240
KFYYIYNEKG LEVTITARFL YGKKVEGTAF VIFGIQDGEQ RISLPESLKR IPIEDGSGEV   300
VLSRKVLLDG VQNPRAEDLV GKSLYVSATV ILHSGSDMVQ AERSGIPIVT SPYQIHFTKT   360
PKYFKPGMPF DLMVFVTNPD GSPAYRVPVA VQGEDTVQSL TQGDGVAKLS INTHPSQKPL   420
SITVRTKKQE LSEAEQATRT MQALPYSTVG NSNNYLHLSV LRTELRPGET LNVNFLLRMD   480
RAHEAKIRYY TYLIMNKGRL LKAGRQVREP GQDLVVLPLS ITTDFIPSFR LVAYYTLIGA   540
SGQREVVADS VWVDVKDSCV GSLVVKSGQS EDRQPVPGQQ MTLKIEGDHG ARVVLVAVDK   600
GVFVLNKKNK LTQSKIWDVV EKADIGCTPG SGKDYAGVFS DAGLTFTSSS GQQTAQRAEL   660
QCPQPAARRR RSVQLTEKRM DKVGKYPKEL RKCCEDGMRE NPMRFSCQRR TRFISLGEAC   720
KKVFLDCCNY ITELRRQHAR ASHLGLARSN LDEDIIAEEN IVSRSEFPES WLWNVEDLKE   780
PPKNGISTKL MNIFLKDSIT TWEILAVSMS DKKGICVADP FEVTVMQDFF IDLRLPYSVV   840
RNEQVEIRAV LYNYRQNQEL KVRVELLHNP AFCSLATTKR RHQQTVTIPP KSSLSVPYVI   900
VPLKTGLQEV EVKAAVYHHF ISDGVRKSLK VVPEGIRMNK TVAVRTLDPE RLGREGVQKE   960
DIPPADLSDQ VPDTESETRI LLQGTPVAQM TEDAVDAERL KHLIVTPSGC GEQNMIGMTP  1020
TVIAVHYLDE TEQWEKFGLE KRQGALELIK KGYTQQLAFR QPSSAFAAFV KRAPSTWLTA  1080
YVVKVFSLAV NLIAIDSQVL CGAVKWLILE KQKPDGVFQE DAPVIHQEMI GGLRNNNEKD  1140
MALTAFVLIS LQEAKDICEE QVNSLPGSIT KAGDFLEANY MNLQRSYTVA IAGYALAQMG  1200
RLKGPLLNKF LTTAKDKNRW EDPGKQLYNV EATSYALLAL LQLKDFDFVP PVVRWLNEQR  1260
YYGGGYGSTQ ATFMVFQALA QYQKDAPDHQ ELNLDVSLQL PSRSSKITHR IHWESASLLR  1320
SEETKENEGF TVTAEGKGQG TLSVVTMYHA KAKDQLTCNK FDLKVTIKPA PETEKRPQDA  1380
KNTMILEICT RYRGDQDATM SILDISMMTG FAPDTDDLKQ LANGVDRYIS KYELDKAFSD  1440
RNTLIIYLDK VSHSEDDCLA FKVHQYFNVE LIQPGAVKVY AYYNLEESCT RFYHPEKEDG  1500
KLNKLCRDEL CRCAEENCFI QKSDDKVTLE ERLDKACEPG VDYVYKTRLV KVQLSNDFDE  1560
YIMAIEQTIK SGSDEVQVGQ QRTFISPIKC REALKLEEKK HYLMWGLSSD FWGEKPNLSY  1620
IIGKDTWVEH WPEEDECQDE ENQKQCQDLG AFTESMVVFG CPN                   1663
```

BIOMARKERS FOR COGNITIVE DYSFUNCTION DISEASES AND METHOD FOR DETECTING COGNITIVE DYSFUNCTION DISEASE USING BIOMARKERS

CROSS-REFERENCE TO RELATED APPLICATIONS

This application is a Divisional of co-pending application Ser. No. 16/890,739, filed on Jun. 2, 2020, which is a Divisional of application Ser. No. 14/901,275, filed on Dec. 28, 2015, now abandoned, which is the National Phase under 35 U.S.C. § 371 of International Application No. PCT/JP2013/067785, filed on Jun. 28, 2013, all of which are hereby expressly incorporated by reference into the present application.

REFERENCE TO AN ELECTRONIC SEQUENCE LISTING

The content of the electronic sequence listing titled "4877-0128PUS3_Sequence_Listing.xml", size: 5,532 bytes, Date of Creation: Jul. 8, 2023, is herein incorporated by reference in its entirety.

TECHNICAL FIELD

The present invention relates to biomarkers which are novel proteins and peptides capable of being employed for detecting cognitive dysfunction diseases including mild cognitive impairment and Alzheimer's disease, and methods for detecting cognitive dysfunction diseases using the biomarkers.

BACKGROUND ART

A major prior art as a means for using samples exhibiting in vivo conditions which are normal and are not normal for determining a difference between them is a technology employed generally in extracorporeal diagnostic agents.

Most of the extracorporeal diagnostic agents are employed in diagnosis in which blood constituents are analyzed as biomarkers.

The prior art in this field involves blood tests to quantify a single certain protein or oligopeptide having a molecular weight of 10,000 or less, or to determine the activity in cases of enzymatic proteins, thereby identifying a marked difference between the normal sample (healthy individual) and the disease sample, which serves as an aid in the diagnosis.

Thus, a certain number of biological samples from healthy and diseased individuals are assayed for levels or activities of a single or multiple certain proteins or certain oligopeptides to determine the abnormal and normal ranges. Then, a biological sample to be evaluated is measured by the same method and the evaluation is made based on the range, abnormal or normal, in which the measured value is included.

Typical measurement methods include an enzyme linked immunosorbent assay (ELISA) in which the levels of a single or multiple certain proteins or peptides in a sample which has been or has not been diluted preliminarily is measured based on the colorimetric level of the sample using a specific primary antibody or secondary antibody labeled with an enzyme which develops a color when reacting with a substrate, as well as a chemiluminescent immunoassay (CLIA). Those also included are a radioimmunoassay (RIA) which measures the aforementioned certain protein or peptide levels using a radioisotope bound to the primary antibody or the secondary antibody and an enzyme activity assay, when the protein is an enzyme, in which a substrate is added directly and the resultant products are measured based, for example, on color development.

Another method employs an analysis of an enzymatic degradation product from a substrate using a high pressure liquid chromatography (HPLC). Alternatively, HPLC is combined with a mass spectrometer in an LC-MS/MS method, which is then also utilized in a selected reaction monitoring (SRM)/multiple reaction monitoring (MRM) method.

In a still another method, a sample is pretreated appropriately and then subjected to a two-dimensional polyacrylamide gel electrophoresis (2D-PAGE) to separate proteins or peptides, and thereafter the intended protein or peptide is subjected to a silver staining, coomassie blue staining, or immunostaining employing a relevant antibody (western blotting), thereby measuring the concentration in the sample.

Alternatively, a biological sample is fractionated by a column chromatography and a fraction is subjected to a mass spectrometry to analyze the proteins and the peptides contained therein.

Instead of the column chromatography, a pretreatment using a protein chip is conducted for a mass spectrometry, or a pretreatment using magnetic beads is conducted for a mass spectrometry.

The inventor also had developed an immunoMS method in which beads (including magnetic beads) are allowed to bind to an antibody against the target protein or peptide, thereby capturing the target protein or peptide which are thereafter allowed to elute from the beads and measured by the mass spectrometry.

Also for the purpose of analyzing an intact protein, a method was reported in which the aforementioned method is used to conduct a mass spectrometry after degradation, for example, with trypsin (see Patent Document 1).

Nevertheless, in any of the aforementioned method, a direct fractionation is conducted utilizing the nature of an intact protein, or a specifically adsorbing protein molecule is selected for mass spectrometric analysis.

Cognitive dysfunction diseases, a representative of which is Alzheimer's disease, are prevailing rapidly also in Japan in response to an increase in the population of the aged. The population was about 1,300,000 in 1995, and then increased to about 2,800,000 in 2010, and is assumed to approximate 4,100,000 in 2020. The Alzheimer's disease is believed to account for 60 to 90% of the cognitive dysfunction diseases. This disease is becoming a social problem because it makes a patient suffer not only from loss of memory but also from destruction of personality, thereby impairing the social life function of the patient.

In Japan, donepezil hydrochloride, which is an anti-acetylcholine esterase inhibitor, was approved in the end of 1999, and it became possible, by an early administration, to retard the decrease in the cognitive function at a high probability. In Alzheimer's disease, an early diagnosis is a greatest challenge for achieving the effectiveness of current therapeutic methods or drugs which will be developed in future.

The followings are the major diagnostic criteria for Alzheimer's disease (DSM IV) made by American Psychiatric Association.

A. The development of multiple cognitive deficits manifested by both:
   (1) memory impairment (impaired ability to learn new information or to recall previously learned information)
   (2) one or more of the following cognitive disturbances:
      a) aphasia (language disorder)
      b) apraxia (impaired ability to carry out motor activities despite intact motor function)
      c) agnosia (failure to recognize or identify objects despite intact sensory function)
      d) disturbance in executive functioning (i.e., planning, organizing, sequencing, abstracting)
B. The cognitive deficits in Criteria A(1) and A(2) each cause significant impairment in social or occupational functioning and represent a significant decline from a previous level of functioning (Non-Patent Document 1).

There are various diseases associated to Alzheimer's disease (AD). Since a cognitive disease such as AD exhibits a slowly developing reduction in the cognitive functions, there is a condition which should be referred to as precursory condition of the cognitive disease. Such a condition is referred to as a mild cognitive impairment (MCI). Based on the statistic data in United states, MCI in hospital visitors for amnesia is advanced to AD within 1 year in 10 to 15% of the patients, and within 4 years in about 50%. The precursory condition of AD is mostly included in amnesic MCI.

According to the current definitions, MCI is regarded as a condition in which complaint relating to a reduction in the cognitive functions is given but there is no particular difficulty in everyday life. Frontotemporal dementia (FTD) is characterized by reduced cognitive functions together with a selfish behavior regardless of the circumstance, and is in contrast with AD in which a patient makes an effort to be in harmony with the circumstance. FTD includes Pick's disease in which a pick body is observed histologically in cerebral cortex.

Dementia with Lewy Bodies (DLB) is characterized by progressive memory disturbance and visual cognitive impairment such as hallucination. Based on the diagnosis of clinical signs, 10 to 30% of cognitive disease is DLB, whose morbidity is second highest after Alzheimer-type cognitive disease (AD) among senile degenerative cognitive disease types. Histologically, Lewy Body is present characteristically in cerebral cortex. Since FTD and DLB exhibit a cognitive disease and are of a dementia type, they are referred to also as dementia-type neurological diseases (Non-Patent Document 1).

Tests employed widely in diagnosing the cognitive disease are Revised Hasegawa's Dementia Scale (HDS-R) and MMSE (Mini-Mental State Examination) in which questions are given to a subject and the diagnosis is made based on the answers. HDS was revised in 1991 and then became to be referred to as HDS-R.

This is constituted from questions in 9 terms, which are intended to test orientation, encoding, calculation ability, memory/recall, and common sense. 23 points or less on a maximum scale of 30 points are considered to be reflecting a suspected cognitive disease. On the other hand, MMSE was established in United States for diagnosing dementia and involves orientation, memorizing ability, calculation ability, speech ability, understanding of diagrams, and the like. It gives 11 questions and 23 points or less on a maximum scale of 30 points, similarly to HDS-R, are considered to be reflecting a suspected cognitive disease. The results of the both tests are believed to be in a relatively good agreement with each other. These question-based diagnostic methods are employed merely for screening, and do not give any definitive diagnoses, and any of HDS-R or MMSE is not employed in classification of severity (Non-Patent Document 1).

Image-based diagnostic methods are CT/MRI which observes morphological abnormality in brain such as encephalatrophy and enlarged vadum and ventricle, single photon emission computed tomography (SPECT) which measures cerebral blood flow level, and positron emission tomography (PET) which measures oxygen consumption/glucose consumption. SPECT and PET are a nuclear medicine-based methods and believed to be capable of detecting abnormality before onset of morphological abnormality (Non-Patent Document 1). Nevertheless, these image-based diagnostic methods have drawbacks due to difficulty in being conducted in every medical facility because of special devices required for them. In addition, they are not sufficient for give an objective decision because the decision differs from physician to physician who observes the image.

As discussed above, the diagnosis of the cognitive disease depends currently on a method which is less objective and requires expensive instruments, and is not successful in screening for identifying the disease. If a biomarker which enables an objective diagnosis using a readily obtainable patient's sample such as blood (including serum and plasma) is found here, a screening can be conducted, thereby enabling an early detection of a cognitive dysfunction disease which is the most challenging in these days.

Patent Document 1 discloses a method for detecting a change in the level of apolipoprotein A-II in a serum of a cancer-carrying mammal in which the quantified levels of the apolipoprotein A-II contained in multiple serum samples derived from the aforementioned identical cancer-carrying mammal are compared with each other among the aforementioned samples.

Patent Document 2 discloses a hepatoma biomarker for detecting a hepatoma consisting of at least one protein or peptide selected from the group consisting of, for example, fibrinogen α chain consisting of the amino acid sequence represented by SEQ ID NO:1 described in this relevant Document 2.

Patent Documents 3 to 5 disclose biomarkers for diagnosis of cognitive dysfunction diseases. Patent Document 5 discloses a biomarker for detecting cognitive dysfunction diseases, which consists of at least one protein or peptide selected from, for example, complement C3 consisting of the amino acid sequence represented by SEQ ID NO:1 described in this relevant Document 5, transthyretin consisting of the amino acid sequence represented by SEQ ID NO:15 described in this relevant Document 5, or a peptide fragment having 5 or more amino acid residues from the aforementioned protein or peptide.

CITATION LIST

Patent Literatures

[Patent Document 1] JP-A No. 2004-333274
[Patent Document 2] JP-A No. 2006-308533
[Patent Document 3] JP-A No. 2010-271078
[Patent Document 4] JP-A No. 2012-037349
[Patent Document 5] JP-A No. 2012-132808

Non-Patent Literature

[Non-Patent Document 1] "YOKUWAKARU ALZHEIMER'S DISEASE", ed. by K. Nakano, H. Mizusawa, Nagai Shoten, 2004

[Non-Patent Document 2] N. Benkirane et al., J. Biol. Chem. Vol. 268, 26279-26285, 1993.

[Non-Patent Document 3] Czepiel, SA, http://czep.net/stat/mlelr.pdf, 2010, Maximum likelihood estimation of logistic regression models: theory and implementation.

[Non-Patent Document 4] Bowling, S R, et al. JIEM, 2009, 2: 114-127, A logistic approximation to the cumulative normal distribution.

SUMMARY OF INVENTION

Technical Problem

An object of the present technology is to provide a biomarker and a method for detecting a cognitive dysfunction disease using the biomarker.

Solution to Problem

The inventor has searched for proteins and their partial peptides which are present or absent or are present in different levels in non-demented control subjects and patients having cognitive dysfunction diseases.

Then, the inventor made an intensive study and discovered three polypeptides capable of detecting cognitive dysfunction diseases in serum. These three polypeptides were identified to be (a) a peptide derived from apolipoprotein A1 consisting of the amino acid sequence represented by SEQ ID NO:1, (b) a peptide derived from transthyretin consisting of the amino acid sequence represented by SEQ ID NO:2, and (c) a peptide derived from complement C3 consisting of the amino acid sequence represented by SEQ ID NO:3.

The inventor also analyzed the combinations of the biomarkers which exhibited high percentages of correct answers in detecting the cognitive dysfunction diseases using a logistic regression analysis. As a result, it was discovered that, among the combinations described above, the combination of two peptides, namely, the aforementioned (c) a peptide derived from complement C3 and the aforementioned (b) a peptide derived from transthyretin or the aforementioned (a) a peptide derived from apolipoprotein A1 can achieve a higher detection accuracy for the cognitive dysfunction diseases (especially mild cognitive dysfunction and Alzheimer's disease).

In the present technology, the non-demented control (NDC) subject includes healthy humans, and means the subjects which may have any diseases but not have cognitive dysfunction diseases (non-demented control).

Also in the present technology, when referring to collectively as cognitive dysfunction diseases, it is intended that mild cognitive impairment (MCI), Alzheimer's disease (AD), and dementia-type neurological diseases are also included. In the present technology, mild cognitive impairment (MCI) and Alzheimer's disease (AD) can preferably be detected.

The peptides identified in the present technology have significance as biomarkers when detected not only in serum but also in other biological samples such as blood, serum, plasma, cerebrospinal fluid, urine, and the like. Similarly, source proteins from which the aforementioned peptides are derived (hereinafter referred to as "intact proteins") or source peptides also have a significance as biomarkers.

Thus, the present technology provides one or more biomarkers for detecting cognitive dysfunction diseases selected from the following (a), (b), and (c):

(a) a biomarker for detecting cognitive dysfunction diseases consisting of an intact protein of apolipoprotein A1 comprising the amino acid sequence represented by SEQ ID NO:1 or a partial peptide thereof;

(b) a biomarker for detecting cognitive dysfunction diseases consisting of an intact protein of transthyretin comprising the amino acid sequence represented by SEQ ID NO:2 or a partial peptide thereof; and, (c) a biomarker for detecting cognitive dysfunction diseases consisting of an intact protein of complement C3 comprising the amino acid sequence represented by SEQ ID NO:3 or a partial peptide thereof.

The present technology provides a method for detecting cognitive dysfunction diseases in which one or more biomarkers for detecting cognitive dysfunction diseases selected from the aforementioned (a) biomarker, (b) biomarker, and (c) biomarker in a biological sample are measured simultaneously or separately.

The present technology provides a kit for detecting cognitive dysfunction diseases for measuring one or more biomarkers for detecting cognitive dysfunction diseases selected from the aforementioned (a) biomarker, (b) biomarker, and (c) biomarker.

The present technology provides a method for selecting a combination of multiple biomarkers for detecting cognitive dysfunction diseases which gives a high percentage of correct answers comprising measuring two or more biomarkers for cognitive dysfunction diseases in a biological sample from a subject, conducting an analysis of the measurement results of each of the aforementioned two or more biomarkers by a logistic regression analysis, and selecting a combination of the biomarkers for detecting cognitive dysfunction diseases which gives a high percentage of correct answers based on the results of the aforementioned analysis.

Advantageous Effects of Invention

According to the present technology, it is possible to provide biomarkers and methods for detecting cognitive dysfunction diseases using the biomarkers.

DESCRIPTION OF EMBODIMENTS

In the present technology, one or more biomarkers selected from the intact proteins described in (a) to (c) shown below and/or the partial peptides thereof can be used for detecting cognitive dysfunction diseases.

(a) A biomarker for detecting cognitive dysfunction diseases consisting of an intact protein of apolipoprotein A1 comprising the amino acid sequence represented by SEQ ID NO:1 or a partial peptide thereof, (b) a biomarker for detecting cognitive dysfunction diseases consisting of an intact protein of transthyretin comprising the amino acid sequence represented by SEQ ID NO:2 or a partial peptide thereof, and, (c) a biomarker for detecting cognitive dysfunction diseases consisting of an intact protein of complement C3 comprising the amino acid sequence represented by SEQ ID NO:3 or a partial peptide thereof.

The present technology can detect, when a subject has a cognitive dysfunction disease, the type and the level of at least one intact protein and/or partial peptide thereof respectively among those described in the aforementioned (a) to (c) in a biological sample.

In addition, the present technology enables a diagnosis of whether the subject has a cognitive dysfunction disease or not at a higher accuracy by detecting at least one intact protein and partial peptide thereof among those described in the aforementioned (a) to (c) in a biological sample simultaneously with measuring the change in the type and the level of them.

The present technology can provide a system for diagnosis and the like whose accuracy and specificity are both extremely high by measuring one or more biomarkers selected from the aforementioned (a) to (c) in a biological sample. As a result, it is possible to conduct a highly accurate diagnosis and the like with regard to the cognitive dysfunction diseases. In addition, the biomarkers of the present technology is highly useful also in judging the efficacy of a drug.

Moreover, by means of measuring the level of each of the biomarkers of the aforementioned (a) to (c), when the intact protein and/or partial peptide thereof among those described in the aforementioned (a) to (c) in a biological sample from a subject is present or increased, the present technology make it possible to, for example, detect, evaluate, discriminate, diagnose, or test that the relevant subject has a cognitive dysfunction disease including mild cognitive impairment or Alzheimer's disease. Furthermore, the present technology allows the diagnosis or the like of whether the subject has a cognitive dysfunction disease or not at a higher accuracy by comparison with a biological sample from a non-demented control subject.

Preferably, two or more of the biomarkers of the aforementioned (a) to (c) are combined to detect the cognitive dysfunction diseases since the accuracy of the detection of the cognitive dysfunction diseases becomes higher. When multiple biomarkers are detected, the detection or diagnosis of the cognitive dysfunction diseases can be made at a high accuracy.

More preferably, two biomarkers, namely, the aforementioned (c) biomarker (C3) and the aforementioned (a) biomarker (ApoA1) or the aforementioned (b) biomarker (TTR) are measured because the accuracy of the detection of the cognitive dysfunction diseases (MCI and AD) becomes higher. When these two biomarkers were detected, there are the cognitive dysfunction diseases (MCI and AD).

It is further preferable, for a further higher detection accuracy, to measure the two biomarkers, namely, the aforementioned (c) biomarker (C3) and the aforementioned (a) biomarker (ApoA1) when the aforementioned cognitive dysfunction disease detection is the mild cognitive impairment detection, or, to measure the two biomarkers, namely, the aforementioned (c) biomarker (C3) and the aforementioned (b) biomarker (TTR) when the aforementioned cognitive dysfunction disease detection is the Alzheimer's disease detection.

As used herein, a "peptide" of a "partial peptide of an intact protein" of the present technology is meant to include a "polypeptide" and an "oligopeptide".

The aforementioned "oligopeptide" generally has a molecular weight of 10,000 or less and consists of amino acids bound to each other, or has several to about 50 amino acid residues or less.

The aforementioned "polypeptide" generally has a molecular weight of 10,000 or more and consists of amino acids bound to each other, or has about 50 amino acid residues or more.

In the present technology, a partial peptide of an intact protein is a peptide having a partial amino acid sequence which is a part of the amino acid sequence possessed by the intact protein.

This partial peptide of an intact protein may sometimes be formed as a partial peptide during expression and synthesis through transcription and translation, or sometimes be formed as a digestion product due to an in vivo digestion after being synthesized as an intact protein. This may be due to deregulation of the mechanism for synthesis and control of the protein in the presence of in vivo condition which is not normal, as in a cognitive dysfunction disease or the like.

The present technology enables evaluation, discrimination, and the like of whether a subject is in a normal condition or is having a cognitive dysfunction disease by using an in vivo protein expression and synthesis and/or digestion as an index, and also enables, in case of having the cognitive dysfunction diseases, evaluation, discrimination, and the like of the degree to which the disease has been advanced.

In the present technology, "detection of cognitive dysfunction diseases" means detection of whether a subject has a cognitive dysfunction disease or not, and otherwise it may be evaluation, discrimination, diagnosis or test, and the like. The detection of the cognitive dysfunction diseases of the present technology may include evaluation or the like of the risk at which the subject will have a more serious cognitive dysfunction.

In the present technology, the intact protein capable of being employed as a biomarker for detecting cognitive dysfunction diseases may, for example, be apolipoprotein A1 comprising the amino acid sequence represented by SEQ ID NO:1, transthyretin comprising the amino acid sequence represented by SEQ ID NO:2, and complement C3 comprising the amino acid sequence represented by SEQ ID NO:3.

A partial peptide of these intact proteins can be employed also as a biomarker for detecting cognitive dysfunction diseases.

"The partial peptide of an intact protein" in the present technology is meant to include the intact protein as well as a peptide fragment having 5 or more amino acid residues generated from a peptide formed during synthesis and degradation thereof.

The partial peptide of an intact protein capable of being employed as a biomarker for detecting cognitive dysfunction diseases may, for example, be a polypeptide consisting of the amino acid sequence represented by SEQ ID NO:1 (preferably apolipoprotein A1-derived polypeptide), a polypeptide consisting of the amino acid sequence represented by SEQ ID NO:2 (preferably transthyretin-derived polypeptide), and a polypeptide consisting of the amino acid sequence represented by SEQ ID NO:3 (complement C3-derived polypeptide).

The present technology can employ, as a biomarker, a protein or peptide consisting of an amino acid sequence resulting from deletion, substitution, or addition of one or several amino acids in each amino acid sequence of the proteins described in the aforementioned (a) to (c) and partial peptides thereof.

As used herein, "one or several" means "one to three", "one or two", and "one".

In the present technology, a partial peptide employed as a biomarker is meant to include a protein or a peptide comprising the amino acid sequence represented by SEQ ID NOs:1 to 3 as well as peptide fragments generated therefrom having 5 or more amino acid residue.

The reason why "5 or more amino acid residues" is designated in a "peptide fragment having 5 or more amino acid residues" in the present technology is based on the description in Non-Patent Document 2. This Non-Patent Document 2 reports that a peptide resulting from substituting K for R in the histone H3's C-terminal (130 to 135) amino acid residue sequence IRGERA and a peptide CGG-GERA resulting from deletion of IR and ligation of CGG to GERA were recognized by an antibody obtained by using peptide IRGERA as an immunogen. This reflects that the recognition of the antigenicity is accomplished by a peptide consisting of 4 or more amino acid residues.

While, in the present technology, the number of the residues is 5 or more which is larger by one to ensure a more general coverage rather than limiting to histone H3's C-terminal, it is important to cover even such a low molecular peptide when the detection or separation is conducted by an immunological procedure such as immunoblotting, ELISA, immunoMS method, and the like.

To an intact protein or its partial peptide, a sugar chain may be added. Such a protein or its partial peptide to which a sugar chain was added can also be used as a biomarker for detecting cognitive dysfunction diseases.

In the present technology, a biomarker may be quantified, or a qualification can be conducted to determine the presence or absence. In such a case, when the biomarker concentration is not lower than a predetermined measured value or when it is not lower than the normal value in the group having no cognitive dysfunction, it is possible to, for example, detect or diagnose that there is a cognitive dysfunction disease. Also by the biomarker quantification, it is possible to, for example, detect or diagnose whether the case is positive/negative, and, when there was a reaction with the biomarker and a color was developed or the like, then the case is judged as positive.

As a method for separating a biomarker in a biological sample such as serum in the present technology, a two-dimensional electrophoresis or a two-dimensional chromatography (2D-LC) can be employed. The chromatography employed in the two-dimensional chromatography may be any known chromatography such as ion exchange chromatography, reverse phase chromatography, gel filtration chromatography, and the like.

Also as a method for separating the biomarkers in the present technology, SRM/MRM method employing LC-MS which combines a chromatography (LC) with a triple quadrupole mass spectrometry can be employed for quantification. In such a case, the LC may be a one-dimensional LC.

In addition, the present technology can employ, as a method for separating the biomarkers, an immunoMS method (see Patent Document 1) in which beads (including magnetic beads) the inventor developed are allowed to bind to antibodies against target proteins or peptides, thereby capturing the proteins or peptides to be measured which are then allowed to elute from the beads and then measured by mass spectrometry, which enables a convenient evaluation of the existence or the level of the target proteins, protein fragments, or peptides without employing two-dimensional electrophoresis or chromatography.

The type and the level of one or more proteins in a biological sample can be measured simultaneously or separately by various methods. When the target protein (including protein fragment and its partial peptide) was specified and the antibody against it (primary antibody) was obtained, then the following methods can be employed.

The present technology preferably involves the measurement conducted by at least one of immunoblotting method, western blotting method, enzyme-, fluorescence-, or radioactive-labeling method, mass spectrometry, immunoMS method, and surface plasmon resonance method.

The biomarkers of the present technology also enable a simultaneous or separate measurement even when the types or the levels are different.

In the present technology, it is more preferred to subjecting these proteins and peptides or peptide fragments to 2D-LC-MALDI-TOF-MS method which combines a two-dimensional chromatography with a mass spectrometry, SRM/MRM method, and immunoMS method, thereby measuring a large number of proteins or their partial peptides all at once.

Here, in the present technology, enzyme linked immunosorbent assay (ELISA), chemiluminescent immunoassay (CLIA), radioimmunoassay (RIA), methods employing enzyme activity measurements, and the like are referred to as "enzyme-, fluorescence-, or radioactive-labeling methods". These methods when employing antibodies are referred to as "enzyme-, fluorescence-, or radioactive-labeled antibody method".

1. Immunoblotting Method

This is the simplest method. Serially diluted serum samples are prepared and an aliquot (about 1 microliter) is dropped onto an appropriate membrane such as a nitrocellulose membrane and then dried in air. After treatment with a blocking solution containing a protein such as BSA followed by washing, reaction with a primary antibody, and then washing, a labeled secondary antibody for detecting the primary antibody is reacted. After washing the membrane, the label is visualized and the concentration is measured.

2. Western Blotting Method

After conducting a one-dimensional or two-dimensional gel electrophoresis including isoelectric focusing or SDS-PAGE, the separated protein is once transferred onto an appropriate membrane such as a PVDF membrane, and a primary antibody and a labeled secondary antibody are employed to conduct a procedure analogous to the aforementioned immunoblotting method, thereby measuring the level of the target protein.

3. ELISA Method

An antibody against a protein or its partial peptide is bound to a support such as a microtiter plate which has been modified chemically in a specific manner, and a sample is subjected to a serial dilution, and its appropriate amount is added to the microtiter plate having the antibody bound and then incubated. Thereafter, the protein and the partial peptide which were not captured are washed out. Then, a secondary antibody having a fluorescent or chemiluminescent substance or an enzyme bound thereto is added and incubated.

For detection, each substrate is added and thereafter the fluorescent or chemiluminescent substance or the enzymatic reaction-induced visible light is measured, thereby accomplishing evaluation and judgment. Instead of the antibody, a substance capable of binding to the protein or its partial peptide may be employed. For example, aptamer can be employed.

The present technology preferably employs a substance toward a biomarker described in the aforementioned (a) to (c) (for example, antibody, aptamer, and the like).

Further methods (see Patent Document 2) are also exemplified below, but they are not limitative.

4. Method Employing Microarray (Microchip)

A microarray is a collective name which means a device in which a substance capable of binding to a substance to be measured is immobilized as being aligned (arrayed) on a support (substrate). In the present technology, an antibody against the protein or the partial peptide or an aptamer may be aligned and immobilized.

In the measurement, a biological sample is added to an immobilized antibody and the like, and a protein or a partial peptide to be measured is bound onto the microarray, and then a secondary antibody having a fluorescent or chemiluminescent substance or enzyme bound thereto is added and incubated. For detection, each substrate is added and thereafter the fluorescent or chemiluminescent substance or the enzymatic reaction-induced visible light may be measured.

5. Mass Spectrometry

In a mass spectrometry, for example, an antibody against a certain protein or its partial peptide is bound to a microbead or substrate (protein chip) which has been modified chemically in a specific manner. The microbead may be a magnetic bead. The substrate of any material may be employed.

The antibody employed may be all of (1) an antibody which recognizes only the full-length of a certain protein, (2) an antibody which recognizes only a partial peptide, and (3) an antibody which recognizes both of a certain protein and its partial peptide, or a combination of the aforementioned (1) and (2), (1) and (3), or (2) and (3).

An appropriate amount of the sample is added as it is or after serial dilution with a buffer solution to a microbead or a substrate to which the antibody has been bound, and incubated. Thereafter, the non-captured protein and partial peptide are washed out. Then, the protein and the partial peptide captured on the microbead or the substrate are analyzed by a mass spectrometry using MALDI-TOF-MS, SELDI-TOF-MS and the like, thereby measuring the peak mass numbers and the peak intensities of the protein, protein fragment, and the partial peptide. By adding a predetermined amount of an appropriate internal standard to the starting biological sample, measuring its peak intensity, and calculating the ratio to the peak intensity of the target substance, its concentration in the starting biological sample can be known. Such a method is referred to as an immunoMS method.

It is also possible that a sample is separated by means of HPLC as it is or after diluting it with a buffer solution or removing the protein partly, and quantification can be conducted by a mass spectrometry using an electrospray ionization (ESI) method. In such a case, by means of an absolute quantification by SRM/MRM method employing an isotopically labeled internal standard peptide, the concentration in the sample can be known.

In addition to the aforementioned methods, methods employing two-dimensional electrophoresis and surface plasmon resonance may also be employed in analysis of the protein and the partial peptide.

The present technology also includes a method for detecting cognitive dysfunction diseases using as an index the existence or the level of the aforementioned biomarker by subjecting a biological sample taken from a subject to a two-dimensional electrophoresis or a surface plasmon resonance.

The present technology also includes a device capable of detecting the biomarkers in the aforementioned biological sample (for example, detecting device, measuring device, analyzing device, and the like). The device according to the present technology preferably has an antibody- or aptamer-immobilizing part (capturing part) and a measuring part. The antibody- or aptamer-immobilizing part preferably has a solid support such as a glass slide and 96-well titer plate to which the antibody or aptamer is immobilized. The measuring part preferably has a light detecting means relevant to the detection target, such as a spectrophotometer and fluorescence spectrophotometer.

The device of the present technology may include an analyzing part which analyzes the data obtained, and the analyzing part preferably includes a data processing device and a software for analysis.

In addition, a controlling part including CPU and the like provided in the device disclosed herein or a system capable of being connected thereto (for example, personal computer, computer network system, and the like) is provided with a program capable of conducting the detection, diagnosis, and the like of the cognitive dysfunction diseases of the aforementioned present technology or a memory storing such a program as well as a system.

According to the present technology, it is possible to judge a cognitive dysfunction of a subject. The present technology also allows a cognitive dysfunction of a subject to be evaluated at a mild stage, and thus is useful also in preventive medicine. If a mental therapy or a medication given to a patient having a cognitive dysfunction disease serves to suppress the progression of the impairment, the suppression is reflected on the levels of the proteins/partial peptides in biological samples such as serum. By measuring such levels, the effectiveness of the treatment can be evaluated and judged, and screening for a drug discovery target biomolecule becomes possible.

As shown in Examples described below, the inventor prepared a large number of peptides, to each of which a respective antibody was prepared. Using such an antibody, the biomarkers for detecting the cognitive dysfunction diseases were searched for. For this purpose, an analysis based on a receiver operating characteristic curve (ROC curve) was employed to evaluate the usefulness of each biomarker. As a result, it was discovered that a peptide derived from apolipoprotein A1 consisting of the amino acid sequence represented by SEQ ID NO:1, a peptide derived from transthyretin consisting of the amino acid sequence represented by SEQ ID NO:2, and a peptide derived from complement C3 consisting of the amino acid sequence represented by SEQ ID NO:3 are the markers exhibiting AUCs of 0.6 or more in the analysis based on the receiver operating characteristic curve (ROC curve).

Furthermore, the inventor examined whether the multimarker can be used to distinguish the cognitive dysfunction diseases (MCI and AD) from the healthy subject having no cognitive dysfunction diseases or not. For this purpose, a logistic regression analysis was employed in this examination.

As a result of the analysis of the logistic regression analysis, detection of the cognitive dysfunction diseases at as an extremely high accuracy as about 90% became possible by using transthyretin and complement C3 as multimarkers.

Thus, the present technology can provide a method for selecting a combination of multiple biomarkers for detecting cognitive dysfunction diseases which gives a high percentage of correct answers comprising (i) measuring two or more biomarkers for cognitive dysfunction diseases in a biological sample from a subject, (ii) conducting an analysis of the measurement results of each of the aforementioned two or more biomarkers by a logistic regression analysis, and (iii) selecting a combination of the biomarkers for detecting cognitive dysfunction diseases which gives a high percentage of correct answers based on the results of the aforementioned analysis.

It is preferable here that by using a logistic regression analysis and if the percentage of correct answer for distinguishing MCI when comparing NDC and MCI is preferably 80% or higher, more preferably 85% or higher or if the percentage of correct answer for distinguishing AD when comparing NDC and AD is preferably 85% or higher, more preferably 90% or higher, MCI or AD is distinguished and the biomarkers for detecting it is selected.

It is also possible that, before the aforementioned (i), among the proteins or their partial peptides relating to the cognitive dysfunction diseases in the biological sample from a subject, those exhibiting high AUCs is selected as biomarkers for detecting the cognitive dysfunction diseases based on the analysis by the ROC curve. It is advantageous to select the proteins or their partial peptides exhibiting AUCs of 0.6 or higher as biomarkers for detecting the cognitive dysfunction diseases.

The ROC curve and the logistic regression curve are as described below in Examples.

Consequently, an optimum biomarker combination can be selected and can serve to raise the percentage of correct answer for the cognitive dysfunction diseases in detection, diagnosis, and the like. Accordingly, by measuring the selected multiple biomarkers, it is possible to conduct a more objective and more accurate detection, diagnosis, and the like for the cognitive dysfunction diseases.

Among these combinations, the aforementioned (b) biomarker and the aforementioned (c) biomarker are preferably measured simultaneously or separately and used, based on the consequent measurement results, in detection, diagnosis, and the like of the cognitive dysfunction diseases because of the highest percentage of correct answer.

The method of the present technology can be stored as a program in a hardware resource provided with a controlling part such as CPU and a recording media (USB memory, HDD, CD, DVD, and the like) and can be executed by the controlling part of a testing device, a selecting device, or the like.

The present technology can be utilized also as a cognitive dysfunction disease detection kit using the biomarkers described in the aforementioned (a) to (c).

The present technology may also be a cognitive dysfunction disease detection kit for measuring one or more biomarkers for the detecting cognitive dysfunction diseases selected from the aforementioned (a) biomarker (ApoA1), the aforementioned (b) biomarker (TTR), and (c) biomarker (C3).

Among these, a detection kit combining the (c) biomarker (C3) with the aforementioned (a) biomarker (ApoA1) or the (b) biomarker (TTR) is preferred.

For the purpose of detecting these markers simultaneously or separately, the detection kit of the present technology may be a single-component type cognitive dysfunction detection kit containing all reagents capable of detecting the biomarkers described in the aforementioned (a) to (c) or a cognitive dysfunction disease detection kit having multiple (2 or more) detection kits each having a reagent capable of detecting each biomarker in a discrete container.

This detection kit preferably includes an antibody against each biomarker of the present technology or an aptamer.

In a preferred method for detecting the cognitive dysfunction diseases according to the present technology, one or more biomarkers for detecting cognitive dysfunction diseases selected from the aforementioned (a) biomarker, the aforementioned (b) biomarker, and the aforementioned (c) biomarker in a biological sample are measured simultaneously or separately.

A more preferred method for detecting cognitive dysfunction diseases of the present technology comprises (i) measuring two or more biomarkers for detecting cognitive dysfunction diseases selected from the aforementioned (a) biomarker, the aforementioned (b) biomarker, and the aforementioned (c) biomarker in a biological sample from a subject simultaneously or separately, and (ii) judging that the subject has cognitive dysfunction diseases when at least two or more biomarker measurement results are classified to the cognitive dysfunction diseases.

The present technology also can employ the following constitution.

Thus the technology is as follows.

[1] One or more biomarkers for detecting cognitive dysfunction diseases selected from the following (a), (b), and (c):
  (a) a biomarker for detecting cognitive dysfunction diseases consisting of an intact protein of apolipoprotein A1 comprising the amino acid sequence represented by SEQ ID NO:1 or a partial peptide thereof,
  (b) a biomarker for detecting cognitive dysfunction diseases consisting of an intact protein of transthyretin comprising the amino acid sequence represented by SEQ ID NO:2 or a partial peptide thereof and,
  (c) a biomarker for detecting cognitive dysfunction diseases consisting of an intact protein of complement C3 comprising the amino acid sequence represented by SEQ ID NO:3 or a partial peptide thereof.

[2] A method for detecting cognitive dysfunction diseases comprising measuring one or more biomarkers for detecting cognitive dysfunction diseases selected from the following (a), (b), and (c) in a biological sample simultaneously or separately:
  (a) a biomarker for detecting cognitive dysfunction diseases consisting of an intact protein of apolipoprotein A1 comprising the amino acid sequence represented by SEQ ID NO:1 or a partial peptide thereof,
  (b) a biomarker for detecting cognitive dysfunction diseases consisting of an intact protein of transthyretin comprising the amino acid sequence represented by SEQ ID NO:2 or a partial peptide thereof and
  (c) a biomarker for detecting cognitive dysfunction diseases consisting of an intact protein of complement C3 comprising the amino acid sequence represented by SEQ ID NO:3 or a partial peptide thereof.

[3] The method for detecting cognitive dysfunction diseases according to Claim 2 comprising the following (i) and (ii):
  (i) measuring two or more biomarkers for detecting cognitive dysfunction diseases selected from the following (a), (b), and (c) in a biological sample from a subject simultaneously or separately;
    (a) a biomarker for detecting cognitive dysfunction diseases consisting of an intact protein of apolipoprotein A1 comprising the amino acid sequence represented by SEQ ID NO:1 or a partial peptide thereof;

(b) a biomarker for detecting cognitive dysfunction diseases consisting of an intact protein of transthyretin comprising the amino acid sequence represented by SEQ ID NO:2 or a partial peptide thereof, and (c) a biomarker for detecting cognitive dysfunction diseases consisting of an intact protein of complement C3 comprising the amino acid sequence represented by SEQ ID NO:3 or a partial peptide thereof; and (ii) judging that the subject has cognitive dysfunction diseases when at least two or more biomarker measurement results are classified to the cognitive dysfunction diseases.

[4] The method for detecting cognitive dysfunction diseases according to the aforementioned [2] or [3] comprising measuring two biomarkers, namely, the aforementioned (c) biomarker and the aforementioned (a) biomarker or the aforementioned (b) biomarker.

[5] The method for detecting cognitive dysfunction diseases according to any one of the aforementioned [2] to [4] comprising measuring two biomarkers, namely, the aforementioned (c) biomarker and the aforementioned (a) biomarker when the aforementioned detection of the cognitive dysfunction diseases is the detection of mild cognitive impairment.

[6] The method for detecting cognitive dysfunction diseases according to any one of the aforementioned [2] to [4] comprising measuring two biomarkers, namely, the aforementioned (c) biomarker and the aforementioned (b) biomarker when the aforementioned detection of the cognitive dysfunction diseases is the detection of Alzheimer's disease.

[7] The method for detecting cognitive dysfunction diseases according to any one of the aforementioned [2] to [6] wherein measurement is conducted by at least one of immunoblotting method; western blotting method: enzyme, fluorescence, or radioactive-labeling method; mass spectrometry; immunoMS method; and surface plasmon resonance method.

[8] A cognitive dysfunction disease detection kit for measuring one or more biomarkers for detecting cognitive dysfunction diseases selected from the following (a), (b), and (c):

(a) a biomarker for detecting cognitive dysfunction diseases consisting of an intact protein of apolipoprotein A1 comprising the amino acid sequence represented by SEQ ID NO:1 or a partial peptide thereof;

(b) a biomarker for detecting cognitive dysfunction diseases consisting of an intact protein of transthyretin comprising the amino acid sequence represented by SEQ ID NO:2 or a partial peptide thereof; and (c) a biomarker for detecting cognitive dysfunction diseases consisting of an intact protein of complement C3 comprising the amino acid sequence represented by SEQ ID NO:3 or a partial peptide thereof.

[9] The cognitive dysfunction disease detection kit according to the aforementioned [8] comprising an antibody against the aforementioned biomarker or aptamer.

[10] The cognitive dysfunction disease detection kit according to the aforementioned [8] or [9] wherein the aforementioned antibody or aptamer is immobilized on a substrate.

[11] The cognitive dysfunction disease detection kit according to any one of the aforementioned [8] to [10] having two biomarkers, namely, the aforementioned (c) biomarker and the aforementioned (a) biomarker or the aforementioned (b) biomarker.

[12] The cognitive dysfunction disease detection kit according to any one of the aforementioned [8] to [11] having two biomarkers, namely, the aforementioned (c) biomarker and the aforementioned (a) biomarker when the detection of the aforementioned cognitive dysfunction diseases is the detection of the mild cognitive impairment.

[13] The cognitive dysfunction disease detection kit according to any one of the aforementioned [8] to [11] having two biomarkers, namely, the aforementioned (c) biomarker and the aforementioned (b) biomarker when the detection of the aforementioned cognitive dysfunction diseases is the detection of Alzheimer's disease.

The aforementioned selection kit may be of a single-component type or multiple-component type.

[14] The cognitive dysfunction disease detection kit for conducting the method for detecting cognitive dysfunction diseases according to any one of the aforementioned [2] to [7].

[15] The method for detecting cognitive dysfunction diseases according to any one of the aforementioned [2] to [7] employing the cognitive dysfunction disease detection kit according to any one of the aforementioned [8] to [13].

[16] A method for selecting a combination of multiple biomarkers for detecting cognitive dysfunction diseases which gives a high percentage of correct answers comprising: measuring two or more biomarkers for cognitive dysfunction diseases in a biological sample from a subject; conducting an analysis of the measurement results of each of the aforementioned two or more biomarkers by a logistic regression analysis: and selecting a combination of the biomarkers for detecting cognitive dysfunction diseases which gives a high percentage of correct answers based on the results of the aforementioned analysis.

[17] The method for selecting a combination of biomarkers for cognitive dysfunction diseases according to the aforementioned [16] comprising measuring two or more proteins by a multiplex immunoassay method, preparing ROC curves for comparison of MCI (mild cognitive impairment) vs. NDC (non-demented control) and AD (Alzheimer's disease) vs. NDC (non-demented control), and selecting a protein exhibiting an AUC of 0.6 or higher as a biomarker for cognitive dysfunction diseases.

[18] The method for selecting a combination of biomarkers for cognitive dysfunction diseases according to the aforementioned [16] or [17] wherein the percentage of correct answer for distinguishing MCI when comparing NDC and MCI is 80% or higher, more preferably 85% or higher and/or the percentage of correct answer for distinguishing AD when comparing NDC and AD is 85% or higher, more preferably 90% or higher.

[19] A program for selecting a combination of biomarkers for cognitive dysfunction diseases for allowing a computer to execute the method according to any one of the aforementioned [16] to [18], or a control part or computer which stores the program.

[20] A program for selecting a combination of biomarkers for cognitive dysfunction diseases recorded on a recording media for allowing a computer to execute the method according to any one of the aforementioned [16] to [18], or a control part or computer which stores the program.

[21] A biomarker, detection method, detection kit, or combination selection method according to any one of the aforementioned [1] to [18] wherein the aforementioned biomarkers are one or more selected from the peptide consisting of the amino acid sequence represented by SEQ ID NO:1, the peptide consisting of the amino acid sequence represented by SEQ ID NO:2, and the peptide consisting of the amino acid sequence represented by SEQ ID NO:3.

[22] A biomarker, detection method, detection kit, or combination selection method according to any one of the aforementioned [1] to [18] wherein the aforementioned partial peptide is a partial peptide of an intact protein, or a peptide fragment which is derived from the protein or peptide and which has 5 or more amino acid residues.

The followings are the typical Examples and the like, to which the present invention (present technology) is not limited.

EXAMPLES

Experiment Example 1

<Detection of Cognitive Dysfunction Diseases Markers by Multiplex Immunoassay Method>

Among the marker proteins associated to neurodegenerative diseases including Alzheimer's disease, those of the complement system, namely, complement C3, complement C4, and complement factor H and those involved in suppressing the formation of AB fibers responsible for cerebral amyloidosis, namely, transthyretin and alpha-2-macroglobulin are employed as markers, and the biological samples obtained from study subjects were examined by an immunoassay method, thereby detecting cognitive dysfunction diseases based on the existence or the level of the marker as an index.

As a method for detection, a multiplex immunoassay method which simultaneously detects multiple markers (analytes) in the biological samples was employed.

(1) Serum Samples

The term in each parenthesis is abbreviated hereinafter as indicated just before the parenthesis.

The serum samples obtained from 37 AD (Alzheimer's disease) cases, 22 NDC (subjects having no mental diseases) cases, and 39 MCI (mild cognitive impairment) cases were employed.

(2) Methods

Apolipoprotein E (ApoE), apolipoprotein A1 (ApoA1), complement C3 (C3), tranathyretin (TTR), complement factor H (Factor H), and alpha-2-macroglobulin (Alpha-2-M) were measured using MILLIPLEX(Trade mark) multiplex kit (HNDG1-36K, Merck Millipore Corporation). Complement C4 (C4) was measured using MILLIPLEX (Trade mark) multiplex kit (HNDG2-36K, Merck Millipore Corporation).

(2-1) Preparation of Serum Sample (Serum Sample for Measuring ApoE, ApoA1, C3, TTR, Factor H, and Alpha-2-M)

The serum samples were employed after 40,000-fold dilution. Thus, 5 μl of the serum was added to a 1.5 ml tube, to which 995 μl of the assay buffer was added and stirred gently. A 5 μl aliquot of this diluted solution was taken into another tube, to which 995 μl of the assay buffer was added and stirred gently. The resultant solution was used as an assay sample.

(Serum Sample for Measuring C4)

The serum samples were employed after 2,000-fold dilution. Thus, 5 μl of the serum was added to a 1.5 ml tube, to which 495 μl of the assay buffer was added and stirred gently. A 10 μl aliquot of this diluted solution was taken into another tube, to which 190 μl of the assay buffer was added and stirred gently. The resultant solution was used as an assay sample.

(2-2) Preparation of Diluted Bead Solution

The bead to which an antibody which recognizes the protein to be detected was bound was mixed and diluted to prepare a diluted bead solution.

(Diluted Bead Solution for Measuring ApoE, ApoA1, C3, TTR, Factor H, and Alpha-2-M)

To a bottle for mixing, 2,100 μl of a bead diluent was added and each 150 μl of 6 bead suspensions having respective antibodies bound thereto was also added and stirred. This was employed as a diluted bead solution.

(Diluted Bead Solution for Measuring C4)

To a bottle for mixing, 2,850 μl of the bead diluent was added and each 150 μl of the bead suspension having C4 antibody bound thereto was added and stirred. This was employed as a diluted bead solution.

(2-3) Preparation of QC Sample

250 μl of pure water was added to a bottle containing a protein for quality control, stirred gently and then allowed to stand for 5 to 10 minutes. This was used as a QC sample.

(2-4) Preparation of Standard Sample

The standard samples for calibration curves were prepared by a serial dilution for 6 concentrations. Thus, 250 μl of pure water was added to a bottle containing a standard protein, stirred gently and then allowed to stand for 5 to 10 minutes to obtain a standard solution at the highest concentration. A 50 μl aliquot of this solution was taken into another tube, to which 150 μl of the assay buffer was added and stirred. Then, 50 μl of the diluted solution was taken into another tube, to which 150 μl of the assay buffer was added and stirred. This procedure was repeated 6 times in total. The serial dilutions were 1, 4, 16, 64, 256, 1024, and 4096-fold dilutions.

(2-5) Antigen-Antibody Reactions

A 96-well assay filter plate for measuring ApoE, ApoA1, C3, TTR, Factor H, and Alpha-2-M and a 96-well assay filter plate for measuring C4 were provided separately, and the antigen-antibody reactions were conducted.

200 μl of a wash buffer was added to the 96-well assay filter plate and stirred at room temperature for 10 minutes at 1,200 rpm using a plate shaker (M-BR-022, TAITEC Corporation). Thereafter, the wash buffer was aspirated off using a manifold. To each of all wells employed, 25 μl of the assay buffer was added and 25 μl of the diluted bead solution was also added. Subsequently, to the assay sample well, standard sample well, QC sample well, and background measurement well, each 25 μl of the respective samples was added. To the background measurement well, the assay buffer was added. After sealing the plates, the antigen-antibody reactions were conducted using a plate shaker. The ApoE, ApoA1, C3, TTR, Factor H, and Alpha-2-M measurement plates were subjected to the antigen-antibody reactions at room temperature for 2 hours. The C4 Measurement plate was subjected to the antigen-antibody reaction at 4° C. for 16 hours.

(2-6) Washing and Measurement

After the antigen-antibody reactions, the solutions were aspirated off, and aspiration was further repeated 3 times while adding 200 μl of the wash buffer, thereby washing the beads. After washing, each 25 μl of the detection antibodies was added to every well which was employed and then the plate was sealed and allowed to undergo the secondary antibody reaction by stirring at room temperature for 1 hour using the plate shaker. After the reaction, 25 μl of streptavidin-phycoerythrin was added, sealed, and stirred at room temperature for 30 minutes using the plate shaker. After the reaction, the solution was aspirated off, and aspiration was further repeated 3 times while adding 200 μl of the wash buffer, thereby washing the beads. 100 μl of a sheath fluid was added to each well and stirred at room temperature for 5 minutes, and then subjected to fluorescence measurement using Luminex 200 (Trade mark) (Luminex Corp., USA). For quantification and analysis of the markers in the serum samples, xPONENT 3.1 software (Luminex Corp., USA) was employed and the equation of the standard curve obtained from the standard samples was used for the quantification.

(3) Results

The differential analysis was conducted whether there was any difference in levels of the detected marker proteins across NDC group, MCI group, and AD group in the serum or not. Table 1 shows the p values when each disease group was subjected to a paired t test with a significance level of p<0.05. Complement C3 (C3) exhibited a significant difference in any of NDC vs. MCI, NDC vs. AD, and MCI vs. AD, and was proven to be useful in distinguishing the patients having cognitive dysfunction diseases (MCI, AD) from the non-demented control (NDC) subjects. Apolipoprotein A1 (ApoA1) and transthyretin (TTR) were also proven to be useful in distinguishing the AD patients from NDC. Apolipoprotein E (ApoE), complement factor H (Factor H), alpha-2-macroglobulin (Alpha-2-M), and complement C4 (C4) exhibited no significant difference between any disease groups.

In order to evaluate the extent to which the detected marker proteins are useful, an analysis based on the receiver operating characteristic curve (ROC curve) was conducted. An area under the ROC curve (AUC of ROC) (herein after referred to as AUC) which is closer to 1 reflects a higher usefulness as a biomarker. When the ROC curves based on the comparison of MCI vs. NDC and AD vs. NDC were made and the marker proteins exhibiting AUCs of 0.6 or higher were analyzed, C3, ApoA1, and TTR were found to be the markers exhibiting AUCs of 0.6 or higher. Table 2 shows the AUCs of C3, ApoA1, and TTR for NDC vs. MCI and NDC vs. AD.

Figure 1:
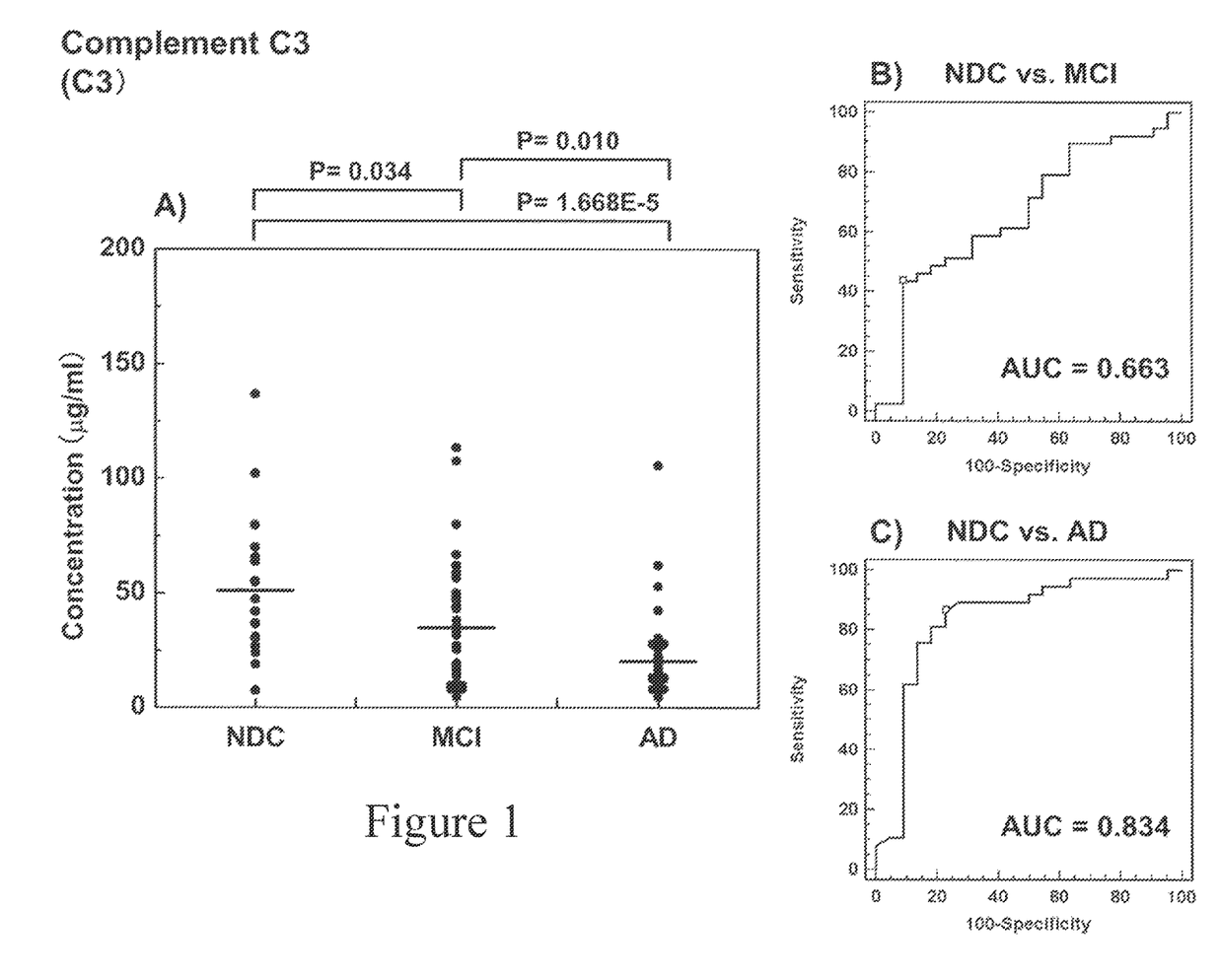
FIG. 1 shows the results of the differential analysis and ROC curves with regard to a marker protein of C3 of SEQ ID NO:3. It includes schematic views showing NDC vs. MCI and NDC vs. AD.
Figure 2:
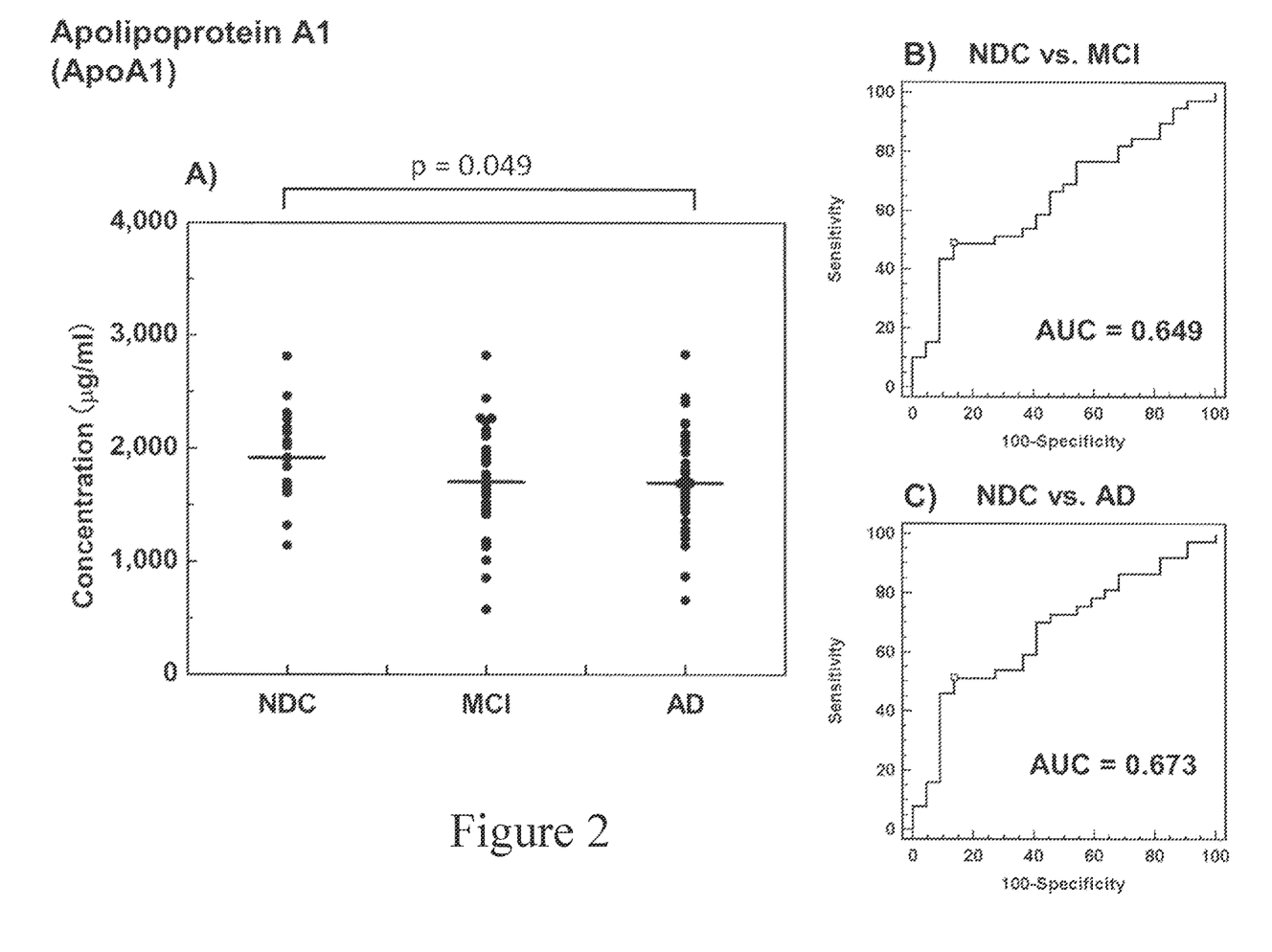
FIG. 2 shows the results of the differential analysis and ROC curves with regard to a marker protein of ApoA1 of SEQ ID NO:1. It includes schematic views showing NDC vs. MCI and NDC vs. AD.
Figure 3:
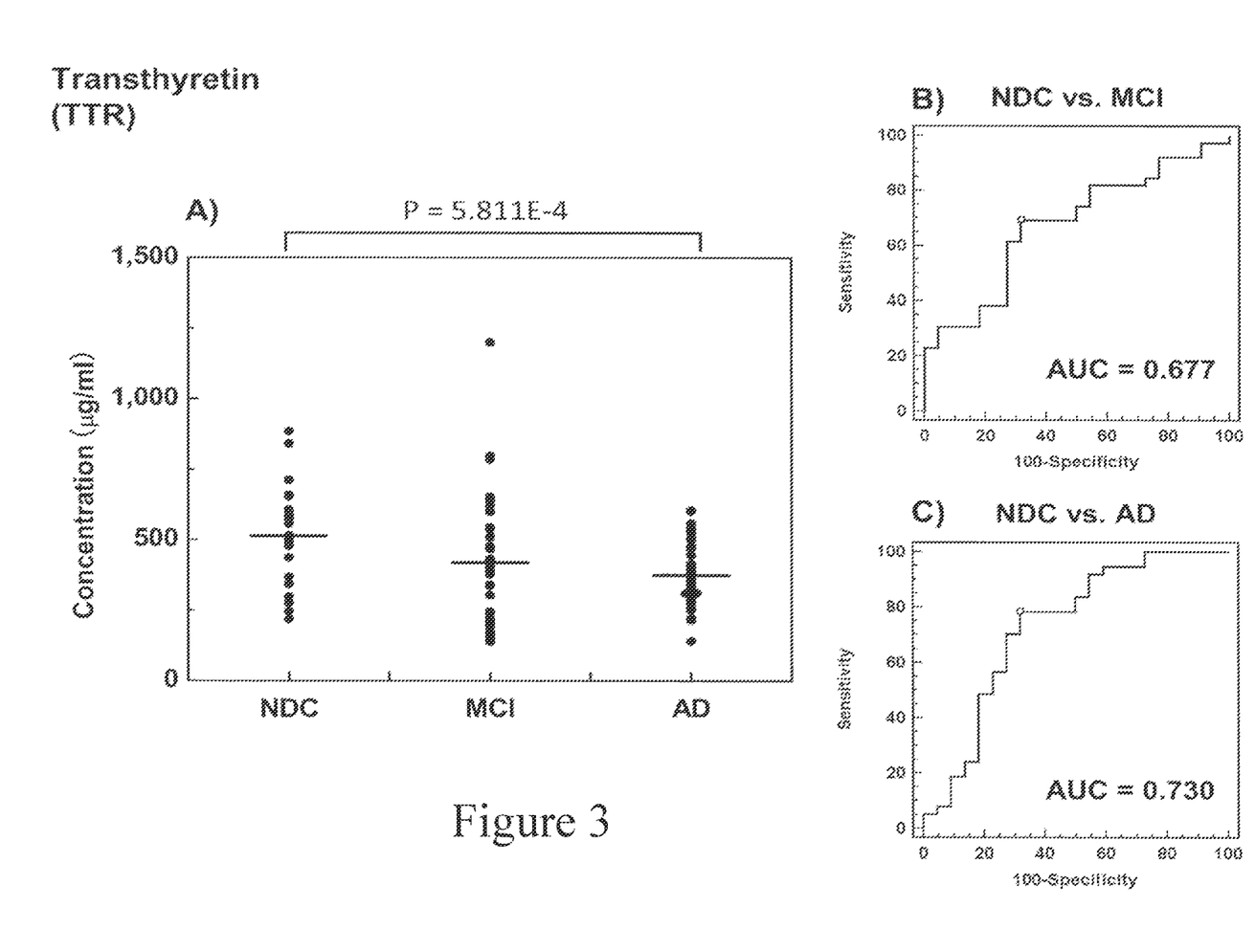
FIG. 3 shows the results of the differential analysis and ROC curves with regard to a marker protein of TTR of SEQ ID NO:2. It includes schematic views showing NDC vs. MCI and NDC vs. AD.

FIGS. 1, 2, and 3 show the differential analyses and the ROC curves with regard to the three marker proteins, namely, C3, ApoA1, and TTR. FIG. 1A) shows a differential analysis diagram, and comparison between NDC and MCI indicates MIC exhibiting a significant reduction in C3 (t test, p value: 0.034) and comparison between NDC and AD indicates AD exhibiting a significant reduction in C3 (t test, p value: 1.668E-4). Comparison between MCI and AD also indicates AD exhibiting a significant reduction in C3 (t test, p value: 0.01). FIG. 1B) and FIG. 1C) show the ROC curves of the comparisons of NDC vs. MCI and NDC vs. AD. The AUC when comparing NDC with MCI was 0.663 while the AUC when comparing NDC with AD was 0.834. FIG. 2A) shows a differential analysis diagram of ApoA1, and comparison between NDC and AD indicates AD exhibiting a significant reduction in C3 (t test, p value: 0.049). FIG. 2B) and FIG. 2C) show the ROC curves of the comparisons of NDC vs. MCI and NDC vs. AD. The AUC when comparing NDC with MCI was 0.649 while the AUC when comparing NDC with AD was 0.673. FIG. 3A) shows a differential analysis diagram of TTR, and comparison between NDC and AD indicates AD exhibiting a significant reduction in C3 (t test, p value: 5.811E-4). FIG. 3B) and FIG. 3C) show the ROC curves of the comparisons of NDC vs. MCI and NDC vs. AD. The AUC when comparing NDC with MCI was 0.677 while the AUC when comparing NDC with AD was 0.730.

For the purpose of analyzing the combination of these three marker proteins, namely, C3, ApoA1, and TTR, which distinguishes MCI or AD from NDC, Experiment Example 2 was conducted.

TABLE 1

| | p value st t-test | | | | | | |
|---|---|---|---|---|---|---|---|
| | C3 | ApoA1 | TTR | ApoE | Factor H | Alpha-2-M | C4 |
| NDC vs. MCI | 0.034 | 0.089 | 0.086 | 0.905 | 0.141 | 0.683 | 0.141 |
| NDC vs. AD | 1.668E−05 | 0.049 | 5.811E−04 | 0.214 | 0.982 | 0.476 | 0.111 |
| MCI vs. AD | 0.010 | 0.902 | 0.265 | 0.206 | 0.153 | 0.231 | 0.883 |

TABLE 2

| | AUC of ROC | |
|---|---|---|
| Marker | NDC vs. MCI | NDC vs. AD |
| C3 | 0.663 | 0.834 |
| ApoA1 | 0.649 | 0.673 |
| TTR | 0.667 | 0.73 |

[1] Apolipoprotein A1-derived peptide (ApoA1)
[Intact protein/peptide]
(SEQ ID NO: 1)

```
0001   MKAAVLTLAV LFLTGSQARH FWQQDEPPQS PWDRVKDLAT VYVDVLKDSG

0051   RDYVSQFEGS ALGKQLNLKL LDNWDSVTST FSKLREQLGP VTQEFWDNLE

0101   KETEGLRQEM SKDLEEVKAK VQPYLDDFQK KWQEEMELYR QKVEPLRAEL

0151   QEGARQKLHE LQEKLSPLGE EMRDRARAHV DALRTHLAPY SDELRQRLAA

0201   RLEALKENGG ARLAEYHAKA TEHLSTLSEK AKPALEDLRQ GLLPVLESFK

0251   VSFLSALEEY TKKLNTQ
```

[2] Transthyretin-derived peptide (TTR)
[Intact protein/peptide]
(SEQ ID NO: 2)

```
0001   MASHRLLLLC LAGLVFVSEA GPTGTGESKC PLMVKVLDAV RGSPAINVAV

005    HVFRKAADDT WEPFASGKTS ESGELHGLTT EEEFVEGIYK VEIDTKSYWK

0101   ALGISPFHEH AEVVFTANDS GPRRYTIAAL LSPYSYSTTA VVTNPKE
```

[3] Complement C3-derived peptide (C3)
[Intact protein/peptide]
(SEQ ID NO: 3)

```
0001   MGPTSGPSLL LLLLTHLPLA LGSPMYSIIT PNILRLESEE TMVLEAHDAQ

0051   GDVPVTVTVH DFPGKKLVLS SEKTVLTPAT NHMGNVTFTI PANREFKSEK

0101   GRNKFVTVQA TFGTQVVEKV VLVSLQSGYL FIQTDKTIYT PGSTVLYRIF

0151   TVNHKLLPVG RTVMVNIENP EGIPVKQDSL SSQNQLGVLP LSWDIPELVN

0201   MGQWKIRAYY ENSPQQVFST EFEVKEYVLP SFEVIVEPTE KFYYIYNEKG

0251   LEVTITARFL YGKKVEGTAF VIFGIQDGEQ RISLPESLKR IPIEDGSGEV

0301   VLSRKVLLDG VQNPRAEDLV GKSLYVSATV ILHSGSDMVQ AERSGIPIVT

0351   SPYQIHFTKT PKYFKPGMPF DLMVFVTNPD GSPAYRVPVA VQGEDTVQSL

0401   TQGDGVAKLS INTHPSQKPL SITVRTKKQE LSEAEQATRT MQALPYSTVG

0451   NSNNYLHLSV LRTELRPGET LNVNFLLRMD RAHEAKIRYY TYLIMNKGRL

0501   LKAGRQVREP GQDLVVLPLS ITTDFIPSFR LVAYYTLIGA SGQREVVADS

0551   VWVDVKDSCV GSLVVKSGQS EDRQPVPGQQ MTLKIEGDHG ARVVLVAVDK

0601   GVFVLNKKNK LTQSKIWDVV EKADIGCTPG SGKDYAGVFS DAGLTFTSSS

0651   GQQTAQRAEL QCPQPAARRR RSVQLTEKRM DKVGKYPKEL RKCCEDGMRE

0701   NPMRFSCQRR TRFISLGEAC KKVFLDCCNY ITELRRQHAR ASHLGLARSN

0751   LDEDIIAEEN IVSRSEFPES WLWNVEDLKE PPKNGISTKL MNIFLKDSIT

0801   TWEILAVSMS DKKGICVADP FEVTVMQDFF IDLRLPYSVV RNEQVEIRAV

0851   LYNYRQNQEL KVRVELLHNP AFCSLATTKR RHQQTVTIPP KSSLSVPYVI

0901   VPLKTGLQEV EVKAAVYHHF ISDGVRKSLK VVPEGIRMNK TVAVRTLDPE

0951   RLGREGVQKE DIPPADLSDQ VPDTESETRI LLQGTPVAQM TEDAVDAERL

1001   KHLIVTPSGC GEQNMIGMTP TVIAVHYLDE TEQWEKFGLE KRQGALELIK

1051   KGYTQQLAFR QPSSAFAAFV KRAPSTWLTA YVVKVFSLAV NLIAIDSQVL

1101   CGAVKWLILE KQKPDGVFQE DAPVIHQEMI GGLRNNNEKD MALTAFVLIS

1151   LQEAKDICEE QVNSLPGSIT KAGDFLEANY MNLQRSYTVA IAGYALAQMG

1201   RLKGPLLNKF LTTAKDKNRW EDPGKQLYNV EATSYALLAL LQLKDFDFVP

1251   PVVRWLNEQR YYGGGYGSTQ ATFMVFQALA QYQKDAPDHQ ELNLDVSLQL

1301   PSRSSKITHR IHWESASLLR SEETKENEGF TVTAEGKGQG TLSVVTMYHA
```

-continued

```
1351    KAKDQLTCNK   FDLKVTIKPA   PETEKRPQDA   KNTMILEICT   RYRGDQDATM

1401    SILDISMMTG   FAPDTDDLKQ   LANGVDRYIS   KYELDKAFSD   RNTLIIYLDK

1451    VSHSEDDCLA   FKVHQYENVE   LIQPGAVKVY   AYYNLEESCT   RFYHPEKEDG

1501    KLNKLCRDEL   CRCAEENCFI   QKSDDKVTLE   ERLDKACEPG   VDYVYKTRLV

1651    KVQLSNDFDE   YIMAIEQTIK   SGSDEVQVGQ   QRTFISPIKC   REALKLEEKK

1601    HYLMWGLSSD   FWGEKPNLSY   IIGKDTWVEH   WPEEDECQDE   ENQKQCQDLG

1651    AFTESMVVFG   CPN
```

Experiment Example 2

<Discrimination of MCI and AD Based on Multimarkers Using Logistic Regression Analysis>

(1) Principle of Logistic Regression Analysis

This method allows the coefficient of each parameter relevant to a biomarker to be obtained from a data set to give the discrimination probability on the patient basis in the two disease categories (normal and disease). A relatively detailed explanation relating to the logistic regression can be obtained from the followings: Non-Patent Document 3: Czepiel, SA, http://czep.net/stat/mlelr.pdf, 2010, Maximum likelihood estimation of logistic regression models: theory and implementation. This explanation includes the analysis based on Newton-Raphson method.

The principle of this analytical procedure is as follows. When assuming the probability of occurrence of a certain event as P, then Equation 1:

$$F(Z) = p = \frac{1}{1+e^{-z}} \quad (1)$$

is known to be approximated to a cumulative standard normal distribution (Non-Patent Document 4: Bowling, S R, et al. JIEM, 2009, 2: 114-127, A logistic approximation to the cumulative normal distribution). Using this approximation, the logistic regression conducts a statistical analysis. As shown below, z is represented as a linear combination of a multivariate $x_i$; i=1,2, ... r.

Equation 2:

$$Z = \beta_0 + \beta_1 x_1 + \beta_2 x_2 + \ldots + \beta_r x_r \quad (2)$$

A large number of data are applied to Equations (1) and (2) to obtain coefficient $\beta_i$, and then whose significance (that $\beta_i$ is not zero) is judged based on the statistic value p.

There are two methods for finalizing Equation (2).

(I) Method Based on Statistic Significance of Coefficient

When a non-significant coefficient was found, then it is excluded to make Equation (2), and the similar application procedure is repeated. When all coefficient of Equation (2) became significant, then, by inserting the measured value of $x_i$, a z value can be obtained from Equation (2). Thereafter, the value of P (discrimination probability) can be obtained from Equation (1). It is also possible to calculate the standard error for the coefficient $\beta_i$.

(II) Method for Obtaining Combination of Coefficients Giving Highest Percentage of Correct Answer The percentage of correct answer is a rate of correct judgment which is the assignment to the group to which the original assignment was made, while, in the method discussed here, all coefficients including coefficients exhibiting no statistical significance are subjected to a trial and error procedure, thereby obtaining the combination giving the highest percentage of correct answer. The discrimination probability is obtained similarly to (I).

The percentage of correct answer of the logistic regression is defined based on the following Equation (3). The discrimination is conducted by assuming, based on the logistic regression equation, which category of the two (for example NDC and MCI) a subject is assigned to. If the category of a subject is i (for example MCI) and the discrimination probability obtained from the logistic regression equation is 0.5 or higher, then it is regarded that a correct diagnosis as i was made. Assuming that the total number of the subjects in Category i is $N_i$ and the number of the subjects diagnosed correctly as i is $C_i$, then Equation 3:

$$\text{Percentage of correct answer} = C_i/N_i \quad (3)$$

represents a percentage of correct answer.

In a logistic regression, the odds ratio to a variate $x_i$ is a value obtained by dividing the odds of when $x_i$ is increased by one unit by the previous odds, and is equal to $\exp(\beta_i)$. An odds ratio of 1 means that the probability of the occurrence of the event discussed here will not change because the odds is same to the previous one even if increasing $x_i$ by one unit. Thus, $\beta_i$ in this case is 0 and there is no contribution to Z. Even when the 95% confidence interval of the odds ratio covers 1, the $\beta_i$ has no statistical significance. It is a matter of course that $\exp(0)=1$.

(2) Logistic Regression Analysis

Among the protein measured by the multiplex immunoassay method in Experiment Example 1, namely, apolipoprotein E (ApoE), apolipoprotein A1 (ApoA1), complement C3 (C3), transthyretin (TTR), complement factor H (Factor H), alpha-2-macroglobulin (Alpha-2-M), and complement C4 (C4), three proteins which exhibited significant differences in the two-group significance tests (t test) of NDC vs. MCI and NDC vs. AD and whose ROC curves had AUCs of 0.6 or higher, namely, C3, ApoA1, and TTR, were selected and subjected to the logistic regression analysis. In the analysis by the logistic regression analysis, a trial and error procedure was employed in including or excluding the marker proteins, and the combination of the marker proteins giving a result showing the highest percentage of correct answer was obtained, and then with this combination, the coefficient of the logistic regression equation (2) (coefficient, $\beta_i$) was calculated.

The logistic regression analysis was executed using MedCalc for Windows(Trade mark), version 9, 2007. (MedCalc Software bvba). This program is based on a Newton-Raphson method.

(3) Results: Combination of Marker Proteins for Distinguishing MCI and Result Showing Highest Percentage of Correct Answer and Logistic Regression Equation's Coefficient Using the combinations of the three marker proteins and the data of the relevant combinations, the logistic regression was conducted and the calculated statistic p values are shown in Table 3. The marker proteins employed in the combinations are indicated with (○), while those not employed are indicated with (•).

TABLE 3

| No. | ApoA1 | TTR | C3 | p value |
|---|---|---|---|---|
| 1 | — | — | ○ | p < 0.05 |
| 2 | — | ○ | — | TTR (p > 0.05) |
| 3 | — | ○ | ○ | p < 0.05 |
| 4 | ○ | — | — | ApoA1 (p > 0.05) |
| 5 | ○ | — | ○ | p < 0.05 |
| 6 | ○ | ○ | — | ApoA1 TTR (p > 0.05) |
| 7 | ○ | ○ | ○ | ApoA1 TTR (p > 0.05) |

When a statistic value p>0.05, the coefficient of the logistic regression equation exhibits no significance. Accordingly, No. 2, 4, 6, and 7 in Table 3 were excluded from calculation of the coefficients. Among the combinations of No. 1, 3, and 5 in Table 3, the combination of marker proteins giving a result showing the highest percentage of correct answer and the coefficient of the logistic regression equation are shown in Table 5. The marker proteins giving a result showing the highest percentage of correct answer when combined are complement C3 (C3) and apolipoprotein A1 (ApoA1), and the coefficient of the relevant logistic regression equation of C3 was −0.02567 and that of ApoA1 was −0.001653, and the constant was 4.6667. The percentage of correct answer for distinguishing MCI when comparing NDC with MCI was 89.74%, and the percentage of correct answer for NDC was 50%.

(4) Results: Combination of Marker Proteins for Distinguishing AD and Result Showing Highest Percentage of Correct Answer and Logistic Regression Equation's Coefficient Using the combinations of the three marker proteins and the data of the relevant combinations, the logistic regression was conducted and the calculated statistic p values are shown in Table 4. The marker proteins employed in the combinations are indicated with (○), while those not employed are indicated with (•).

TABLE 4

| No. | ApoA1 | TTR | C3 | p value |
|---|---|---|---|---|
| 1 | — | — | ○ | p < 0.05 |
| 2 | — | ○ | — | p < 0.05 |
| 3 | — | ○ | ○ | p < 0.05 |
| 4 | ○ | — | — | ApoA1 (p > 0.05) |
| 5 | ○ | — | ○ | ApoA1 (p > 0.05) |
| 6 | ○ | ○ | — | ApoA1 (p > 0.05) |
| 7 | ○ | ○ | ○ | ApoA1 (p > 0.05) |

When a statistic value p>0.05, the coefficient of the logistic regression equation is not significant. Accordingly, No. 4, 5, 6, and 7 in Table 4 were excluded from calculation of the coefficients. Among the combinations of No. 1, 2, and 3 in Table 4, the combination of marker proteins giving a result showing the highest percentage of correct answer and the coefficient of the logistic regression equation are shown in Table 6. The marker proteins giving a result showing the highest percentage of correct answer when combined are complement C3 (C3) and transthyretin (TTR), and the coefficient of the relevant logistic regression equation of C3 was −0.0465 and that of TTR was −0.00564, and the constant was 4.5218. The percentage of correct answer for distinguishing AD when comparing NDC with AD was 91.89%, and the percentage of correct answer for NDC was 68.18%.

TABLE 5

Coefficients and Standard Errors

| Variable | Coefficient | Std. Error | p value |
|---|---|---|---|
| ApoA1 | −0.001653 | 0.0007481 | 0.02713 |
| C3 | −0.02567 | 0.01077 | 0.01713 |
| Constant | 4.6667 | | |

Odds Ratios and 95% Confidence Intervals

| Variable | Odds Ratio | 95% CI |
|---|---|---|
| ApoA1 | 0.9983 | 0.9969 to 0.9998 |
| C3 | 0.9747 | 0.9543 to 0.9954 |

Classification table

| | Predicted group | | |
|---|---|---|---|
| Actual group | NDC | MCI | Percent correct |
| NDC (n = 22) | 11 | 11 | 50.00% |
| MCI (n = 39) | 4 | 35 | 89.74% |
| Percent of cases correctly classified | | | 75.41% |

TABLE 6

Coefficients and Standard Errors

| Variable | Coefficient | Std. Error | P value |
|---|---|---|---|
| TTR | −0.00564 | 0.002451 | 0.02139 |
| C3 | −0.0465 | 0.01615 | 0.003973 |
| Constant | 4.5218 | | |

Odds Ratios and 95% Confidence Intervals

| Variable | Odds Ratio | 95% CI |
|---|---|---|
| TTR | 0.9944 | 0.9896 to 0.9992 |
| C3 | 0.9546 | 0.9248 to 0.9853 |

Classification table

| | Predicted group | | |
|---|---|---|---|
| Actual group | NDG | AD | Percent correct |
| NDC (n = 22) | 15 | 7 | 68.18% |
| AD (n = 37) | 3 | 34 | 91.89% |
| Percent of cases correctly classified | | | 83.05% |

INDUSTRIAL APPLICABILITY

When multiple biomarkers of the present disclosure are used, the accuracy of the detection of cognitive dysfunction diseases including mild cognitive impairment and Alzheimer's disease becomes high, and application to use in the field of diagnosis including diagnostic reagents becomes possible.

The invention claimed is:

1. A method for detecting and treating mild cognitive impairment to slow the progression to Alzheimer's disease comprising
measuring the level of each of three biomarkers (a), (b), and (c) in plasma, serum, or blood in a subject at the level of complement C3 and the level of Transthyretin of 37.4 μg/ml or less and 476.9 μg/ml or less, respectively, or the level of complement C3 and the level of Apolipoprotein A1 of 37.4 μg/ml or less and 1805 μg/ml or less, respectively by an anti-Complement C3 antibody, an anti-Apolipoprotein A1 antibody, and an anti-Transthyretin antibody; wherein,
said biomarker (a) consists of an intact protein of Apolipoprotein A1 comprising the amino acid sequence represented by SEQ ID NO: 1 or a partial peptide thereof,
said biomarker (b) consists of an intact protein of Transthyretin comprising the amino acid sequence represented by SEQ ID NO:2 or a partial peptide thereof, and said biomarker (c) consists of an intact protein of Complement C3 comprising the amino acid sequence represented by SEQ ID NO:3 or a partial peptide thereof;

wherein the subject is determined as having mild cognitive impairment based on a combination of the level of complement C3 and the level of Transthyretin or a combination of the level of complement C3 and the level of Apolipoprotein A1 by a data processing device, wherein the data processing device is configured to calculate at least one regression equation to determine that the subject has mild cognitive impairment, and the data processing device comprises a memory part storing a program, wherein the program makes the controlling part conduct the determining step, the at least one regression equation comprises a combination of coefficients, and all the coefficients are obtained based on levels of the three biomarkers obtained by conducting the measuring step on a group of non-demented controls, a group of those having mild cognitive impairment, wherein the level of complement C3 and the level of Transthyretin of the subject are 37.4 µg/ml or less and 476.9 µg/ml or less, respectively, or the level of complement C3 and the level of Apolipoprotein A1 of the subject are 37.4 µg/ml or less and 1805 µg/ml or less, respectively; and administering to said subject a medication to suppress the progression of said impairment.

2. The method for detecting and treating mild cognitive impairment according to claim 1, wherein (a) said intact protein of Apolipoprotein A1 comprises the amino acid sequence represented by SEQ ID NO:1, (b) said intact protein of Transthyretin comprises the amino acid sequence represented by SEQ ID NO:2; and (c) said intact protein of Complement C3 comprises the amino acid sequence represented by SEQ ID NO:3.

3. The method for detecting and treating mild cognitive impairment according to claim 2, wherein said an anti-Complement C3 antibody, said anti-Apolipoprotein A1 antibody, and said anti-Transthyretin antibody are each immobilized on a solid support.

4. The method for detecting and treating mild cognitive impairment according to claim 3, wherein said measuring step is conducted by use of a spectrophotometer.

5. The method for detecting and treating mild cognitive impairment according to claim 4, wherein the controlling part is configured to calculate the at least one regression equation to obtain a value, and to determine whether that the subject has mild cognitive impairment on the basis of the value, and wherein said at least one regression equation includes Equation 2 to obtain the value for coefficient $\beta_i$, wherein said Equation 2 is:

$$Z=\beta_0+\beta_1 x_1+\beta_2 x_2+\ldots+\beta_x, \quad (2).$$

6. The method for detecting mild cognitive impairment according to claim 1, wherein the percentage of correct answer for the regression equation for determining the subject has MCI is 89.74% or more.

7. The method for detecting mild cognitive impairment according to claim 1, wherein the controlling part comprises CPU that is configured to conduct the determining step.

* * * * *